United States Patent [19]

Lindley et al.

[11] Patent Number: 5,045,336
[45] Date of Patent: Sep. 3, 1991

[54] METHOD OF MODIFYING SWEET TASTE

[75] Inventors: Michael G. Lindley, Crowthorne; Elner B. Rathbone, Wokingham, both of England

[73] Assignee: Amstar Sugar Corporation, New York, N.Y.

[21] Appl. No.: 865,926

[22] Filed: May 14, 1986

Related U.S. Application Data

[63] Continuation of Ser. No. 719,493, Apr. 4, 1985, abandoned.

[30] Foreign Application Priority Data

Apr. 12, 1984 [GB] United Kingdom ................. 8409514

[51] Int. Cl.$^5$ ................................................ A23L 1/22
[52] U.S. Cl. ..................................... 426/534; 426/536; 426/537; 426/538
[58] Field of Search ................ 426/534, 536, 537, 538

[56] References Cited

U.S. PATENT DOCUMENTS 4,544,565 10/1985 Barnett ................................ 426/538
4,567,053 1/1986 Lindley ................................ 426/538
4,642,240 2/1987 Barnett et al. ...................... 426/538

OTHER PUBLICATIONS

Arctauder, Perfume and Flavor Chemicals, vol. II, 1969, Publ. by the Author: Montclair; N. J., Monograph Nos. 2463-2466.
Furia et al., Fenaroli's Handbook of Flavor Ingredients, vol. 2, 1975, CRC Press; Cleveland, Oh., p. 470.
Donald W. Pfaff, "Taste, Olfaction, and the Central Nervous System", The Rockefeller University Press, New York, 1985, pp. 220-223.

*Primary Examiner*—Joseph Golian

[57] ABSTRACT

The sweetness of an ingestible product or oral composition containing a sweetening sugar or sugar alcohol in relatively large quantities can be reduced and thereby the flavor enhanced by incorporation of at least one compound of the general formula (I)

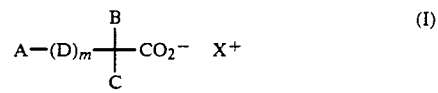

in which m represents 0.1; A represents a homocyclic or heterocyclic aromatic group with one or more rings; and B represents a hydrogen atom, a lower aliphatic group with 1-3 carbon atoms or a phenyl group; or, when m represents O, A and B together represent a bivalent homocyclic or heterocyclic aromatic group with two or more rings, or a methylidene group carrying as a substituent a homocyclic or heterocyclic aromatic group with one or more rings; an aromatic ring of A, or of A and B together, optionally carrying one to three substituents selected from lower alkoxy groups, lower alkyl or alkenyl groups, formyl or acetyl groups, hydroxy groups or acyloxy groups, and halogen atoms; C represents a hydrogen atom or an alkyl group or, when m represents O, a hydroxy or alkoxy group;
D represents a oxygen or sulphur atom;
$X^+$ represents a hydrogen ion or another physiologically compatible cation;

with the proviso that m represents 1 when S represents a substituted or unsubstituted phenyl group and B and C both represent hydrogen atoms; or when A represents an unsubstituted phenyl group, B represents an alkyl group and C represents a hydrogen atom.

20 Claims, No Drawings

METHOD OF MODIFYING SWEET TASTE

This is a continuation of application Ser. No. 719,493, filed Apr. 4, 1985, and now abandoned.

This invention relates to the use of a series of aromatic carboxylic acids and their salts as taste modifiers and sweetness inhibitors and to compositions containing them together with sweet sugars, etc, and which possess a lower degree of sweetness and thus an enhanced flavour as compared with corresponding compositions in which they are not included.

Sugar, i.e. sucrose, is used not only as a sweetener, but is also an essential structural ingredient of many food products, especially in the field of confectionery. In the manufacture of chocolate and various sweets and candies, and various baked goods, e.g. biscuits and cakes, it is often desired to increase the sugar content of the composition but a limit is reached beyond which the product becomes too sweet or sickly. Similarly, the antimicrobial action of sugar is exhibited only at certain high levels, e.g. in jams and preserves. The shelf-life of other products, such as cakes, could be extended if the sugar content were increased. Also, the presence of sugars helps to provide flowability in frozen or chilled products and could provide desirable bulking and texture in savoury goods if the sweetness were somehow removed. There is thus a need for a way of reducing the sweetness of high sugar products so that a pleasant flavour can be obtained while the sugar content is kept high for functional and nutritional reasons. A sugar such as sucrose, has properties which, were it not for the sweetening power, would render it of considerable interest in savoury food products such as soups, sauces and snack products and also "moist" pet foods. A sucrose which had "lost" its sweetness would thus be highly desirable in other food areas than confectionery. Increased sugar content at the expense of fat may also be possible in some products by the use of non-sweet sugar as a less-calorific diluent so that a lower calorie product is obtained. Other sweet sugars are similarly useful in part for their technical properties, for example glucose syrups and lactose.

Another area in which the sweetness of sugars can be a problem is in the supply of carbohydrate to patients suffering from renal problems. Conventionally a concentrated glucose syrup is taken orally. This product is however difficult to take in quantity because of its sickly nature. Attempts have been made to render it more palatable with various flavourings. A less sweet product is clearly of considerable interest to the consumer.

Another problem arises in connection with lactose. This moderately sweet sugar is used as a carrier for flavourings to be added to foodstuffs etc., but its sweetness precludes its use for savoury flavours. Reduction or elimination of the sweetness would render lactose useful in this also.

Finally, other sweet substances allied to sugars, such as the sugar alcohols, are useful for purposes not related to their sweetness, for example humectants such as sorbitol. Beyond a certain level, these substances contribute a degree of sweetness which might be undesirable in some formulations.

U.K. patent application GB 2 066 639A describes and claims the substitution of sucrose in food products by isomaltulose, in order to reduce the sweetness. Such a process, of course, requires the manufacture of isomaltulose itself, which is generally obtained by enzymic isomerisation of sucrose. The incorporation of large quantities of isomaltulose into a food product must therefore, inevitably, increase the cost of the sugar content of the foodstuff. This technique obviously cannot be applied in the case of the glucose syrups mentioned above.

An alternative approach to the problem is to include in the foodstuff composition an ingredient which is designed to counteract the sweetness of the sugar. Thus, for example, the Virginia Dare Extract Company, Inc. of Brooklyn N.Y., U.S.A. are now marketing a blend of natural ingredients under the trade mark Contrasweet, for incorporation into confections such as creams, liquid centres, caramels, icings and fillings, fondants, fudges, hard candies etc. The problem with such a blend of natural ingredients, however, is that, apart from the fact that the sweetness-decreasing effect is limited, the material is bitter and strongly coloured and has a tendency to impart undesirable taste and colour to pale products, particularly icings and fillings.

We have previously found that a particular class of non-toxic, substantially colourless, phenylalkanoic acid salts can effectively reduce the sweetness of sucrose and other sweeteners by 80% or even more when present in relatively small amounts. Our copending British Patent Application No. GB. 2139470A discloses a method of reducing the sweetness of an ingestible product containing a sweetening sugar or sugar alcohol by incorporating therein a sweetness-reducing amount of at least one phenylalkanoic or phenylpyruvic acid salt of the general formula:

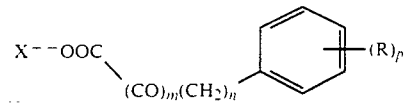

in which m represents 0 or 1, and when m represents 0, n represents 1, 2 or 3, and p represents 1, 2, 3 or 4, and when m represents 1, n represents 1 or 2 and p represents 0, 1, 2, 3 or 4; the substituents R, which may be the same or different, each represent a lower alkoxy group, e.g. with 1 to 5 carbon atoms such as a methoxy, ethoxy, isopropoxy or t-butoxy group, a phenoxy group or a lower alkyl or trifluoromethyl group; and/or two substituents R together represent an aliphatic chain linked to the phenyl ring at two positions; either directly or via an oxa-group, e.g. an alkylenedioxy, alkenylenedioxy, alkylenoxy or alkenylenoxy group; and/or one substituent R represents a hydroxy group while at least one other substituent R represents an alkoxy group; and $X^+$ represents a physiologically acceptable cation.

We have now found that a related but chemically distinct class of carboxylates also possesses the power to inhibit sweetness.

According to the present invention, there is provided a method of reducing the sweetness of an ingestible product containing a sweetening sugar or sugar alcohol by incorporating therein a sweetness-reducing amount of at least one compound of the general formula

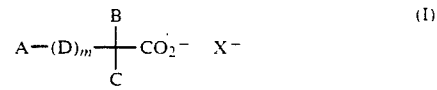

in which m represents 0 or 1; A represents a homocyclic or heterocyclic aromatic group with one or more rings; and B represents a hydrogen atom, a lower aliphatic group with 1-3 carbon atoms or a phenyl group; or, when m represents 0, A and B together represent a bivalent homocyclic or heterocyclic aromatic group with two or more rings, or a methylidene group carrying as a substituent a homocyclic or heterocyclic aromatic group with one or more rings; an aromatic ring of A, or of A and B together, optionally carrying one to three substituents selected from lower alkoxy groups, lower alkyl or alkenyl groups, formyl or acetyl groups, hydroxy groups or acyloxy groups, and halogen atoms;

C represents a hydrogen atom or lower alkyl group or, when m represents 0, a hydroxy or alkoxy group;

D represents an oxygen or sulphur atom;

$X^+$ represents a hydrogen ion or another physiologically compatible cation;

with the proviso that m represents 1 when A represents a substituted or unsubstituted phenyl group and B and C both represent hydrogen atoms; or when A represents an unsubstituted phenyl group, B represents an alkyl group and C represents a hydrogen atom.

By an "ingestible product" there is meant one which in the ordinary course of use is intended to be swallowed, for instance, a foodstuff or beverage, or an orally administered pharmaceutical composition.

In the compound of the general formula (I), $X^+$ preferably represents either a proton (i.e. the compound is in the form of the free acid) or else an alkali metal, alkaline earth metal, or ammonium cation, especially the sodium ion and also the potassium or calcium ion.

The compounds of the general formula I essentially comprise two related series of compounds: those in which m represents 0 and those in which m represents 1. Of the two series, we find that although both are of considerable utility as taste modifiers and sweetness reducers, it is the series in which m represents 1 which are more important in their effects. The compounds are all ethers or thioethers of acetic acid derivatives.

One particularly preferred series of compounds are those of the general formula

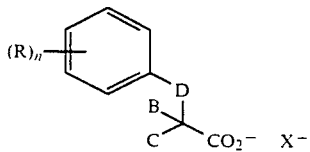

(Ia)

in which B represents a hydrogen atom, an alkyl group with 1 to 3 carbon atoms or a phenyl group; C represents an alkyl group with 1 to 3 carbon atoms or a hydrogen atom; D represents an oxygen or a sulphur atom; R represents an alkoxy group, an alkyl or alkenyl group, a hydroxy group or acyloxy group, a halogen atom, an acetyl group or a formyl group; n represents 0, 1, 2 or 3 and when n represents 2, the two substituents R can together represent a fused phenyl ring as in a naphthyl group; and $X^+$ is as defined for formula I.

In one particularly preferred group of compounds of formula Ia, n represents 1 and the substituent R is at the 2- or 4- position.

In the series of compounds of formula I, in which m represents 0, A preferably represents a phenyl or naphthyl group, or a nitrogen-containing heterocyclic group such as an indolyl (especially the indol-3-yl) group.

Also advantageous are those compounds of formula I where A and B together represent a benzylidene (phenylmethylene) or biphenyl structure (e.g. in cinnamic acid derivatives and fluorene-9-carboxylic acid derivatives respectively). In the formula I, B preferably represents a hydrogen atom, an alkyl group with 1-3 carbon atoms, e.g. an ethyl or isopropyl group, or a phenyl group. C generally represents a hydrogen atom or lower alkyl group, but may represent a hydroxy or alkoxy group.

Particularly preferred compounds for use according to the present invention thus include 1. (±)-2-phenoxypropionic acid, (C.A. 940-31-8)
1(a). S-(−)-2-phenoxypropionic acid, (C.A. 1912-23-8)
2. (±)-2-phenoxybutyric acid, (C.A. 13794-14-4)
2(a). S-(−)-2-phenoxybutyric acid (C.A. 19128-85-9)
3. (±)-2-p-methoxyphenoxybutyric acid, (C.A. 67648-60-6)
4. (±)-2-p-methylphenoxypropionic acid (C.A 22504-83-2)
4(a). S-(−)-2-p-methylphenoxypropionic acid (Fredga & Backstrom, *Arkiv. Kemi*, 25, 455 (1966)
5. (±)-2-p-ethylphenoxypropionic acid (C.A 24431-28-5)
6. (±)-2-p-methoxyphenoxypropionic acid, (C.A. 13794-15-5)
6(a). S-(−)-2-p-methoxyphenoxypropionic acid, (C.A. 4276-74-8)
7. 2-p-methoxyphenoxy-2-methylpropionic acid, (C.A. 17509-51-5)
8. (±)-2-p-ethoxyphenoxypropionic acid, (GB. Pat. 916242)
9. p-methylphenoxyacetic acid, (C.A. 940-64-7)
10. phenoxyacetic acid (C.A. 122-59-5, acid C.A. 3598-16-1, salt)
11. p-methoxyphenoxyacetic acid (C.A. 1877-75-4)
12. p-ethoxyphenoxyacetic acid (C.A. 5327-91-3)
13. (±)-2-p-chlorophenoxypropionic acid (C.A. 3307-39-9)
13(a). S-(−)2-p-chlorophenoxypropionic acid (C.A. 20421-35-6)
14. 2-phenoxy-2-methylpropionic acid (C.A. 943-45-3)
15. 2,4-dimethylphenoxyacetic acid (C.A. 13334-49-1)
16. p-acetylphenoxyacetic acid (C.A. 1878-81-5)
17. p-isopropylphenoxyacetic acid (from Lancaster Synthesis Ltd)
18. p-ethylphenoxyacetic acid (C.A. 24431-27-4)
19. p-formylphenoxyacetic acid (C.A. 22042-11-3).

Other compounds of the formula I showing activity include:

β-naphthyloxyacetic acid, 2-(p-chlorophenoxy)-2-methylpropionic acid, 3,4-dichlorophenoxyacetic acid, p-chlorophenoxyacetic acid, 2-(2-methyl-4-chlorophenoxy)-acetic acid, 2-(3-chlorophenoxy)-propionic acid, 4-fluorophenoxyacetic acid, 2,3-dichlorophenoxyacetic acid, 3-methylphenoxyacetic acid, 2-(3,4-dimethoxyphenoxy)-propionic acid, 2-(2,3,4-trimethoxyphenoxy)-propionic acid, 2-(2,3,4-trimethoxyphenoxy)-butyric acid, 2-methylphenoxyacetic acid, 2-formylphenoxyacetic acid, 2-hydroxyphenoxyacetic acid, 4-iodophenoxyacetic acid, 2-methoxyphenoxyacetic acid, 2-prop-2-enylphenoxyacetic acid, diphenylacetic acid, diphenylhydroxyacetic acid (diphenylglycolic acid), 2-p-chlorophenylpropionic acid, α-naphthylacetic acid, β-naphthylacetic acid, 2-p-isopropylphenylpropionic acid, 2-(2,4-dimethoxyphenyl)-2-methoxyacetic acid, 2-(2,4-dimethylphenyl)-propionic acid, 2-(2-methylphenyl)-propionic acid, 2-(2-phenylphenyl)-butyric acid, 2-(2-methylphenyl)-3-methylbutyric acid, 3,4-dimethoxycinnamic acid, phenylthioacetic acid, fluorene 9-carboxylic acid, indol-3-ylacetic acid.

All of these compounds are known compounds and are listed, for example, in the catalogue of Aldrich Co. Ltd.

Alternatively, compounds of the general formula (I) may be synthesised by condensation and other standard techniques known in this art. For example; carboxylates can be obtained from the corresponding nitriles or alcohols; cinnamic acid derivatives by condensation of the corresponding benzaldehyde derivative; etc.

General references to the synthesis of alkoxyalkanoic acids are:
1. C. F. Koelsch, J. Amer. Chem. Soc. 53, 304 (1931);
2. R. Brettle, J. Chem. Soc., 1891 (1956);

These procedures involve the reaction of the appropriate phenol with a haloalkanoic acid (reference 1) or an ester of a haloalkanoic acid (reference 2).

It will be appreciated that many of the compounds of formula I or Ia are optically active, having a chiral centre adjacent to the carboxyl group. Optical isomers may be obtained either by stereospecific synthesis, or by resolution. A general reference to resolution techniques is P. Newman, Optical Resolution Procedures for Chemical Compounds, Vol 2, 1981, Optical Resolution Information Center N.Y. Compounds such as 2-(p-methoxyphenoxy)-propionic acid can be resolved by brucine salt crystallisation.

It is an interesting finding that in general one enantiomer of the two is much more active than the other so that the racemic mixture is of intermediate activity. We find, for example, that the S-(−)-enantiomers of some compounds of formula (I) (and especially formula (Ia) appear to possess twice the potency as taste and sweetness modifiers compared with the racemic mixtures, suggesting that the R-(+)-enantiomers possess little or no potency. However, it is not yet known whether it is always the case that the S-entantiomer or the (−)-enantioner will always be the more active isomer. It is, however, a simple matter to compare any pair of enantiomers for relative sweetness-modifying power.

We have found that the compounds of the general formula (I) are effective, for example, at a level of about 0.0001 to 0.1% by weight of the composition, especially about 0.0005 to 0.05% e.g. about 0.001 to 0.01%. Except at very high levels of sucrose, the ratio of inhibitor to sweetener is relevant and a range of about 0.01 to 0.2 part by weight per hundred parts by weight of sucrose is effective. At this level, for example 0.1 part per 100 parts of sucrose, compounds such as 2-p-methoxyphenoxypropionic acid, 2-p-methoxyphenoxybutyric acid and 2-p-methyl phenoxypropionic acid or their sodium salts give a reduction in sweetness of over 50% when applied to a 5% sucrose solution. On a molar basis, about 0.0005 to 0.002 mole of compound of formula (I) or (Ia) per mole of sucrose is required. Lesser sweetness reductions can obviously be obtained by incorporating the compound of formula (I) at lower levels. For other sweeteners, for example, a high glucose or fructose syrup, a similar effect can be obtained at a sweetness-related level, that is to say at a level similar to that used to reduce the sweetness of a corresponding amount of sucrose. However, the main commercial interest will obviously lie in use with sucrose. The compounds of use according to this invention do not diminish other flavours present in a foodstuff and do not discolour the product. In fact, we have found that the flavour is enhanced. For example, the incorporation of a relatively small amount of one of the compounds (e.g. about 0.0001 to 0.005%) into a high-sucrose product such as jam can lead to improved fruit flavours.

The compounds of the general formula (I) are non-toxic and substantially tasteless. In rats they have an $LD_{50}$ of well over 5 g/Kg (no deaths at this level).

The compounds were tested according to the following protocol:

A small taste panel was selected on the basis of each member's ability to recognise and distinguish accurately various concentrations of sucrose. The panel was then asked to estimate the sweetness of test samples in the form of sucrose solutions containing the test compound.

These are, of course, model aqueous solutions and do not bear a close resemblance to actual product situations where fat, protein, starch and other ingredients are present and can influence perception of sweetness. A cake, for example, may contain about 25% sucrose but an aqueous solution at this concentration would be strongly sweet.

The following Examples illustrate the invention further:

EXAMPLE 1

Madeira Cake

S-(−)-2-p-Methoxyphenoxypropionic acid was added at a level of 0.05 g (i.e. about 0.0036% overall) to the following mix, after addition of the egg.

| | |
|---|---|
| High ratio fat | 198 g |
| Cake flour | 283 g |
| Caster sugar | 418 g |
| Salt | 7 g |
| Baking powder | 12.5 g |
| Mill powder | 4.5 g |
| Milk powder | 184 g |
| Vanilla essence | 9.5 g |
| Egg | 269 g |

The fat and sugar were creamed together and the eggs beaten in. The flour and other dry ingredients were then folded in and the mixture baked. These cakes were not noticeably sweeter than "normal" recipe cakes containing only 368 g sugar. The increased sugar content extends the shelf life, but its sweetness is reduced to normal.

EXAMPLE 2

Royal Icing 2 egg whites
400 g icing sugar (sieved)
5 ml glycerine.

The egg whites were beaten and the icing sugar mixed in gradually until smooth. The glycerine was then beaten in and sodium 2-p-methylphenoxypropionate was added at 0.005% by weight. At this level of inhibitor, the icing was noticeably less sweet than a control. The effect was less marked than in cakes.

EXAMPLE 3

Butter Icing/filling 100 g butter
100 g icing sugar (sieved)
10 ml hot water.

The fat and sugar were creamed, the water was mixed in, and flavour added (e.g. cocoa dissolved in water and cooled). Sodium 2-naphthoxyacetate was dissolved in a small amount of water and incorporated into the icing at 0.07% by weight.

The icing containing 0.07% inhibitor was obviously less sweet than a control containing no inhibitor.

EXAMPLE 4

Boiled Sweets (lemon)

| | |
|---|---|
| 325 g | sucrose |
| 175 g | glucose syrup: 42 DE |
| 100 g | water |
| 7 g | malic acid |
| 1 ml | oil of lemon flavouring. |

The water and sugar were boiled, the glucose syrup added at 110° C., and temperature increased to 145° C. Sodium diphenylacetate was added at 0.05% by weight or sodium p-ethylphenoxypropionate was added at 0.001% by weight.

The mixture poured onto an oiled marble slab, the acid and flavouring were kneaded in, and the mass was then cut into individual sweets.

EXAMPLE 5

Toffee

| | |
|---|---|
| 120 g | Sucrose |
| 120 g | Full cream condensed milk |
| 120 g | Glucose syrup: 42 DE |
| 50 g | Hard fat (m.p 32° C.) |
| 12 g | Butter |
| 0.13 g | Vanillin |
| 1.0 g | Salt |

All the ingredients except vanillin and butter were heated slowly to dissolve, then cooled to a temperature of 130° C. The vanillin and butter added on removing from heat, together with sodium 2-p-methoxyphenoxybutyrate at 0.005% by weight, and the mass was poured onto an oiled slab, allowed to cool, and cut.

EXAMPLE 6

Transformed sucrose product

A sucrose syrup was transformed into a microcrystalline solid by the process of UK Patent No. 1460614 (U.S. Pat. No. 3,972,725). The syrup contained 90% sucrose by weight plus 0.1% of sodium 2-p-ethoxyphenoxypropionate. The product was a dry, friable, particulate product which could be used in a range of bakery and confectionery applications.

A glucose solid can be obtained from a glucose syrup containing the same inhibitor, by the process of UK Patent 2070015.

EXAMPLE 7

Savory wholemeal biscuits

A conventional semi-sweet recipe comprises:

| | |
|---|---|
| Biscuit flour | 1000 g |
| Wholemeal flour | 250 g |
| Sucrose | 270 g |
| Treacle | 50 g |
| Shortening | 235 g |
| Salt | 15 g |
| Sodium bicarbonate | 3.5 g |
| Ammonium bicarbonate | 4.4 g |
| Water | 130 g |

Addition to the dough mix of 0.5 g (0.023%) of 2-p-methoxyphenoxypropionic acid eliminated the sweetness, allowing the incorporation of savoury ingredients such as cheese and onion.

EXAMPLE 8

Canned pie filling

Addition of about 0.0005% by weight of 2-p-methylphenoxypropionic acid enhances the fruit flavour and cuts the sweetness.

EXAMPLE 9

Bakery Jam

Addition of about 0.0005% by weight of 2-p-methoxyphenoxypropionic acid to a commercial raspberry jam led to an enhanced fruit flavour.

EXAMPLE 10

Intermediate moisture pet food

A moist pet food has the composition:

| | |
|---|---|
| meat and meat by products | 35 parts by weight |
| soy flakes | 35 |
| sucrose | 15 |
| 1,3-butane diol or glycol | 10 |
| milk solids | 5 |
| fat | 2 |
| salt | 2 |
| colour | 0.5 |
| vitamin supplement | 0.5 |

Addition of about 0.05 parts by weight of 2-p-methoxyphenoxypropionic acid provides enhanced acceptability to cats.

EXAMPLE 11

Instant Soup Mix

| | |
|---|---|
| Potato Starch | 28 parts by weight |
| Non-fat dry milk solids | 19 |
| Salt | 14 |
| Hydrolysed starch | 12 |
| Freeze dried chicken | 9 |
| Chicken fat | 9 |
| Monosodium glutamate | 4 |
| Sugar | 8 |
| Hydrolysed vegetable protein | 2 |
| Butter | 1 |
| Onion powder | 0.8 |
| Celery powder (in sugar) | 0.4 |
| Vanilla | 0.4 |
| Parsley | 0.2 |
| Pepper | 0.03 |
| Turmeric | 0.02 |
| 2-p-methoxyphenoxyacetic acid | 0.025 |

The sugar acts as a dispersant without providing sweetness.

EXAMPLE 12

Sweet beverages, e.g. liqueurs and vermouths etc.

High sugar content beverages can be rendered less sweet and the flavour enhanced by addition of about 0.001–0.002% of 2-p-methoxyphenoxypropionic acid.

EXAMPLE 13

Savoury Chewing Gum

| Chewing gum base | 24% by weight |
| --- | --- |
| Sucrose | 60 |
| 42 DE glucose | 14 |
| Glycerol | 1 |
| Flavour/colour | 1 |
| 2-p-methylphenoxypropionic acid | 0.1 |

Inclusion of the last ingredient enables flavours such as chicken, beef, onion or cheese to be added.

EXAMPLE 14

Savoury Ice Cream

| Cream (40% fat) | 2 kg |
| --- | --- |
| Sweetened condensed milk | 2 kg |
| Whole milk | 5 liters |
| Skim milk powder | 0.2 kg |
| Sucrose | 0.7 kg |
| Stabiliser | 30 g |
| Monoglyceride | 30 g |
| Egg Yolk | 200 g |
| Flavour (as required) | |
| 2-p-methoxyphenoxypropionic acid | 2.5 g |

EXAMPLE 15

Orally administered high calorie feed

| 42 DE glucose syrup of 82° Bx | 113.6 g |
| --- | --- |
| Water | 107.2 g |
| Anhydrous citric acid | 1.2 g |
| Sodium benzoate | 0.1 g |
| Sodium 2-p-methoxyphenoxypropionate | 0.05–.01 g |

EXAMPLE 16

Flavour carrier

Lactose (100 parts) was spray dried with savoury flavour such as beef, chicken, cheese, etc. and 2-p-ethylphenoxypropionic acid (0.001 part), which level was sufficient to inhibit the sweetness of the lactose. The lactose acts as a non-sweet carrier for savoury flavours whose flavour profile would have been affected by the presence of sweetness.

We claim:

1. A method of reducing the sweetness of an ingestible product containing a sweetening sugar or sugar alcohol by incorporating therein a sweetness-inhibiting amount which is in the range of 0.0005 to 0.1 weight % of at least one compound of the general formula

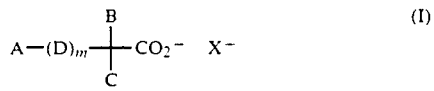

(I)

in which m represents 0 or 1; A represents a substituent selected from the group consisting of a homocyclic and an indolyl group; and B represents a substituent selected from the group consisting of a hydrogen atom, a lower aliphatic group with 1–3 carbon atoms and a phenyl group, and, when m represents O, A and B together may also be selected from the group consisting of a bivalent homocyclic aromatic group and an indolyl group, and a methylidene group carrying a substituent selected from the homocyclic or indolyl groups; an aromatic ring of A, or of A and B together, unsubstituted or carrying one to three substituents selected from the group consisting of lower alkoxy groups, lower alkyl groups, lower alkenyl groups, formyl groups, acetyl groups, hydroxy groups, acyloxy groups, and halogen atoms;

C represents a substituent selected from the group consisting of a hydrogen atom, and a lower alkyl group, when m represents 1, and selected from the group consisting of hydrogen, a lower alkyl group, a hydroxy or alkoxy group when m represents O;

D represents a substituent selected from the group consisting of a oxygen atom and a sulphur atom;

$X^+$ represents a hydrogen ion or another physiologically compatible cation;

with the proviso that m represents 1 when A represents a substituted or unsubstituted phenyl group and B and C both represent hydrogen atoms; and m represents 1 when A represents an unsubstituted phenyl group, B represents an alkyl group and C represents a hydrogen atom.

2. A method according to claim 1, in which the compound incorporated is of the general formula

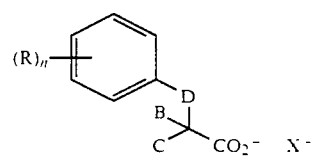

(Ia)

in which B represents a substituent selected from the group consisting of a hydrogen atom, an alkyl group with 1 to 3 carbon atoms and a phenyl group; C represents a substituent selected from the group consisting of an alkyl group with 1 to 3 carbon atoms and a hydrogen atom; D represents a substituent selected from the group consisting of an oxygen and a sulphur atom; R represents a substituent selected from the group consisting of a lower alkoxy group, a lower alkyl group, a lower alkenyl group, a hydroxy group an acyloxy group, a halogen atom, an acetyl group and a formyl group; n represents 0, 1, 2 or 3 and when n represents 2, the two substituents R can together represent a fused phenyl ring; and $X^+$ represents a hydrogen ion or another physiologically compatible cation.

3. A method according to claim 1, in which the compound of formula (I) incorporated is one in which m represents O, A represents a substituent selected from the group consisting of a phenyl group, a naphthyl group and a an indolyl group, B represents substituent selected from the group consisting of a hydrogen atom, an alkyl group with 1–3 carbon atoms and a phenyl group and, together with A a benzylidene group and a biphenyl structure, and C represents a hydrogen atom.

4. A method according to claim 1 in which the compound of formula I incorporated is one in which B and C represent different entities, thus providing a chiral centre, and is present in the form of a racemic mixture or the more active enantiomer.

5. A method according to claim 1 in which the compound of formula I a incorporated is selected from the group consisting of:
($\pm$)-2-phenoxypropionic acid
S-(−)-2-pheoxypropionic acid
($\pm$)-2-phenoxybutyric acid
S-(−)-2-phenoxybutyric acid
($\pm$)-2-p-methoxyphenoxybutyric acid,
($\pm$)-2-p-methylphenoxypropionic acid
(=)-2-phenoxypropionic acid
S-(−)-2-p-methylphenoxypropionic acid
($\pm$)-2-p-ethylphenoxypropionic acid
($\pm$)-2-p-methoxyphenoxypropionic acid
S-(−)-2-p-methoxyphenoxypropionic acid
2-p-methoxyphenoxy-2-methylpropionic acid
($\pm$)-2-p-ethoxyphenoxypropionic acid
p-methylphenoxyacetic acid
phenoxycetic acid
p-methoxyphenoxyacetic acid
p-ethoxyphenoxyacetic acid
($\pm$)-2-p-chlorophenoxypropionic acid
S-(−)2-p-chlorophenoxypropionic acid
−2-phenoxy-2-methylpropionic acid
2,4-dimethylphenoxyacetic acid
p-acetylphenoxyacetic acid
p-isopropylphenoxyacetic acid
p-ethylphenoxyacetic acid
p-formylphenoxyacetic acid.

6. A method according to claim 1, in which the compound is present at a level of 0.0005 to 0.05% by weight.

7. A method according to claim 6, in which the compound is present at a level of 0.001 to 0.01% by weight.

8. A method according to claim 1, in which the compound of the formula Ia is present at a level of 0.01 to 0.2% by weight of the sugar or sugar alcohol present.

9. An ingestible product or oral composition containing a sweetening sugar or sugar alcohol and containing a sweetness inhibiting amount of 0.0005 to 0.1 w % which is in the range of at least one compound of the general formula (I) as defined in claim 1.

10. An ingestible product or oral composition containing a sweetening sugar or sugar alcohol and containing a sweetness inhibiting amount which is in the range of 0.0005 to 0.1 w % of at least one compound of the general formula Ia as defined in claim 2.

11. A product according to claim 10 in the form of a pharmaceutical glucose feed.

12. Sucrose or glucose in the form of a solid or syrup containing a sweetness inhibiting amount of 0.0005 to 0.1 w % which is in the range of at least one compound of the general formula Ia as defined in claim 1.

13. A flavouring agent comprising lactose in combination with a savoury flavouring agent and a sweetness inhibiting amount of 0.0005 to 0.1 w % which is in the range of at least one compound of the general formula Ia as defined in claim 1.

14. A method according to claim 1, in which the compound is S-(−)-2-p-methoxyphenoxypropionic acid.

15. A method according to claim 1 in which $X^-$ represents a physiologically compatible cation other than hydrogen.

16. A method according to claim 2 in which $X^-$ represents a physiologically compatible cation other than hydrogen.

17. A method according to claim 1 in which m is 0.

18. A method according to claim 1 in which B is a lower aliphatic group with 1-3 carbon atoms or a phenyl group.

19. A method according to claim 2 in which B is an alkyl group with 1 to 3 carbon atoms or a phenyl group.

20. A method of reducing the sweetness of an ingestible product containing a sweetening sugar or sugar alcohol by incorporating therein a sweetness inhibiting amount of 0.01 to 0.1% by weight of phenoxyacetic acid.

* * * * *